(12) United States Patent
Blanchard et al.

(10) Patent No.: US 11,701,055 B2
(45) Date of Patent: Jul. 18, 2023

(54) USING PERSONALIZED PHYSIOLOGICAL PARAMETERS FOR SLEEP/WAKE DETECTION

(71) Applicant: BOSE CORPORATION, Framingham, MA (US)

(72) Inventors: Thomas Charles Blanchard, Winchester, MA (US); Darasy Reth, Boston, MA (US)

(73) Assignee: BOSE CORPORATION, Framingham, MA (US)

( * ) Notice: Subject to any disclaimer, the term of this patent is extended or adjusted under 35 U.S.C. 154(b) by 0 days.

(21) Appl. No.: 16/917,071

(22) Filed: Jun. 30, 2020

(65) Prior Publication Data

US 2021/0401363 A1 Dec. 30, 2021

(51) Int. Cl.
*A61B 5/11* (2006.01)
*A61B 5/00* (2006.01)
*A61B 5/0205* (2006.01)

(52) U.S. Cl.
CPC .......... *A61B 5/4809* (2013.01); *A61B 5/0205* (2013.01); *A61B 5/11* (2013.01); *A61B 5/7405* (2013.01); *A61B 2562/0219* (2013.01)

(58) Field of Classification Search
CPC ....... A61B 5/4809; A61B 5/0205; A61B 5/11; A61B 5/7405; A61B 2562/0219; A61B 5/4815; A61B 5/00; A61B 5/48; A61B 5/4806; A61B 5/0022; A61B 5/0533; A61B 5/1118; A61B 7/003; A61B 2560/0242; A61B 5/02055; A61B 5/02405; A61B 5/0245; A61B 5/0816; A61B 5/18; A61B 5/291; A61B 5/352; A61B 5/369; A61B 5/4818; A61B 5/7253; A61B 5/7257;
(Continued)

(56) References Cited

U.S. PATENT DOCUMENTS 9,665,169 B1 5/2017 Dai et al.
2005/0234312 A1 10/2005 Suzuki et al.
(Continued)

FOREIGN PATENT DOCUMENTS

CN 111880423 B * 7/2021 ............. G05B 15/02

OTHER PUBLICATIONS

International Search Report and Written Opinion for International Application No. PCT/US2021/031230 dated Aug. 9, 2021.

*Primary Examiner* — Hai Phan
*Assistant Examiner* — Anthony D Afrifa-Kyei
(74) *Attorney, Agent, or Firm* — Patterson + Sheridan, LLP

(57) ABSTRACT

Aspects of the present disclosure provide methods, apparatuses, and systems for accurately determining sleep and wake onset based on a user's personalized physiological parameters for sleep and wake. First, a user is determined to be asleep using population level data. Thereafter, sensor collected data is used to determine the user's distribution of values of a physiological parameter when the user is asleep. This distribution of values is then used, instead of population-level data, to determine the user is asleep in real-time. As a result, the content and interventions are provided to help users get back to sleep. Further, the described techniques allow more accuracy in determining sleep statistics which can guide recommended interventions and therapies.

12 Claims, 4 Drawing Sheets

(58) Field of Classification Search
CPC .. A61B 5/7264; A61B 5/746; A61M 16/0069; G16H 50/20; G16H 50/30
See application file for complete search history.

(56) References Cited

U.S. PATENT DOCUMENTS

| | | | | |
|---|---|---|---|---|
| 2014/0073486 | A1* | 3/2014 | Ahmed | A61B 5/684 600/479 |
| 2016/0022203 | A1 | 1/2016 | Arnold et al. | |
| 2016/0029904 | A1* | 2/2016 | Quinn | A61B 5/11 600/499 |
| 2016/0151603 | A1* | 6/2016 | Shouldice | A61B 5/4806 600/26 |
| 2019/0030278 | A1 | 1/2019 | Kremer et al. | |
| 2019/0387998 | A1* | 12/2019 | Garten | A61M 21/00 |
| 2020/0178887 | A1* | 6/2020 | Correa Ramírez | A61B 5/746 |
| 2020/0367810 | A1* | 11/2020 | Shouldice | A61B 5/4818 |
| 2021/0124552 | A1* | 4/2021 | Lim | G08B 3/10 |
| 2022/0172836 | A1* | 6/2022 | Neumann | G16H 50/20 |

* cited by examiner

USING PERSONALIZED PHYSIOLOGICAL PARAMETERS FOR SLEEP/WAKE DETECTION

FIELD

Aspects of the present disclosure generally relate to methods, apparatuses, and systems for determining a user is awake or asleep based on personalized, user-specific values of a physiological feature.

BACKGROUND

Wearable devices are used to track activity, monitor health, and help people sleep better. Current sleep detection and sleep tracking methods may estimate a duration of sleep; however, they lack the ability to determine real-time sleep onset or precisely when a user awakes. There is a need to accurately determine when a user falls asleep or wakes up in order to provide a personalized user experience responsive to when the user falls asleep or wakes up.

SUMMARY

Instead of relying primarily on population-level statistics, the methods, apparatuses, and systems described herein use user-specific values of a measured physiological feature to accurately determine when a user has fallen asleep or woken up.

During an initialization stage, population-level statistics are used to determine that a user is, for example, asleep. When the user is determined to be asleep, user-specific physiological parameters are measured and associated with the user being asleep. When the user is determined to be awake, either using population-level statistics or based on user-input indicating the user is awake, user-specific physiological parameters are measured and correlated with the user being awake.

After the initialization stage, during the steady-state stage, the user specific values of the physiological parameters are used to determine, virtually in real-time, whether the user is awake or asleep. In response to determining the user is awake or asleep, one or more actions are taken to provide the user with a customized experience. In an aspect, when the user is determined to be asleep, audio, visual output, and/or haptic output is adjusted by fading out a relaxation or guided breathing exercise or outputting masking sounds. In an aspect, when the user is determined to be awake, the user is prompted to stand up (and get out of bed) to promote better sleep habits or a guided breathing or relaxation exercise is output to help the user fall back asleep.

In an aspect, a method for creating a personalized audio experience is provided. The method includes determining a distribution of user-specific asleep values for a physiological feature when a user is determined to be asleep, determining a distribution of user-specific awake values for the physiological feature when the user is determined to be awake, determining the user is asleep when a measured value of the physiological feature extracted from a real-time physiological signal is in the distribution of user-specific asleep values, determining the user is awake when a measured value of the physiological feature extracted from the real-time physiological signal is in the distribution of user-specific awake values, and altering an audio experience based on determining the user is asleep or awake.

According to aspects, altering the audio experience in response to determining the user is awake comprises initiating an experience to help guide the user to sleep.

According to aspects, the method further comprises determining the user has been awake for a threshold amount of time, wherein altering the audio experience comprises instructing the user to stand up when the user is determined to be awake for the threshold amount of time.

According to aspects, the method further comprises entering a low-power mode by one or more sensors in response to determining the user is asleep.

In an aspect, a method for creating a personalized audio experience is provided. The method comprises, during an initialization stage: measuring a value of a physiological feature associated with a user based on a sensor signal, determining the user is asleep using population-level data and the measured value of the physiological feature, when the user is determined to be asleep, measuring values of the physiological feature extracted from a physiological signal obtained using the sensor signal, determining a distribution of user-specific asleep values based on the measured values of the physiological features, and associating the distribution of user-specific asleep values to the user being asleep; and after the initialization stage: determining the user is asleep when a measured value of the physiological feature extracted from a real-time physiological signal is in the distribution of user-specific asleep values, and altering an audio experience for the user in response to determining the user is asleep based on the measured value of the physiological feature extracted from the real-time physiological signal being in the distribution of user-specific asleep values.

According to aspects, the sensor signal comprises one of: an accelerometer signal, photoplethysmogram (PPG) signal, a radar signal, or any other sensor signal capable of detecting the physiological feature. According to aspects, the physiological signal is a respiration waveform. According to aspects, the physiological feature comprises one of: a respiration rate (RR), ratio of time to inhale to time to exhale, depth of breath, heart rate (HR), heart rate variability (HRV), body movement, or any other physiological feature that changes between wake and sleep.

According to aspects, the initialization stage lasts for a pre-determined amount of time.

According to aspect, the method further comprises one or more sensors entering a low-power mode in response to determining the user is asleep based on the measured value of the physiological feature extracted from the real-time physiological signal being in the distribution of user-specific asleep values.

According to aspects, the method further comprises determining the user is awake when a measured value of the physiological feature extracted from the real-time physiological signal is outside the distribution of user-specific asleep values, and altering the audio experience for the user in response to determining the user is awake.

According to aspects, altering the audio experience for the user in response to determining the user is awake comprises initiating an experience to help guide the user to sleep. According to aspects, altering the audio experience for the user in response to determining the user is awake comprises: in response to determining the user has been awake for a threshold amount of time, instructing the user to stand up. According to aspects, the method further comprises outputting at least one of: time-to-sleep onset or how many times the user awoke during a sleep period.

In an aspect, a method for creating a personalized audio experience is provided. The method comprises, during an initialization stage: measuring a value of a physiological feature associated with a user based on a sensor signal, determining the user is asleep using population-level data and the measured value of the physiological feature, when the user is determined to be asleep, measuring values of the physiological feature extracted from a physiological signal obtained using the sensor signal, determining a distribution of user-specific asleep values based on the measured values of the physiological features, associating the distribution of user-specific asleep values to the user being asleep, determining the user is awake based on user action, when the user is determined to be awake, measuring values of the physiological feature extracted from the physiological signal obtained using the sensor signal, determining a distribution of user-specific awake values based on the measured values of the physiological features, and associating the distribution of user-specific awake values to the user being awake, and after the initialization stage: determining the user is asleep when a measured value of the physiological feature extracted from a real-time physiological signal is in the distribution of user-specific asleep values, determining the user is awake when a measured value of the physiological feature extracted from the real-time physiological signal is in the distribution of user-specific awake values, and altering an audio experience for the user in response to determining the user is one of asleep based on the user-specific distribution of asleep values or awake based on the user-specific distribution of awake values.

According to aspects, the sensor signal comprises one of: an accelerometer signal, photoplethysmogram (PPG) signal, a radar signal, or any other sensor signal capable of detecting the physiological feature. According to aspects, the physiological signal is a respiration waveform. According to aspects, the physiological feature comprises one of a respiration rate (RR), ratio of time to inhale to time to exhale, depth of breath, heart rate (HR), heart rate variability (HRV), body movement or any other physiological feature that changes between wake and sleep.

According to aspects, altering the audio experience for the user in response to determining the user is awake comprises initiating an experience to help guide the user to sleep. According to aspects, altering the audio experience for the user in response to determining the user is awake comprises, in response to determining the user has been awake for a threshold amount of time, instructing the user to stand up.

All examples and features mentioned herein can be combined in any technically possible manner.

DETAILED DESCRIPTION

Sleep plays an important role in overall physical health. As such, it is helpful to understand an individual's sleep statistics such as time to sleep onset, wake after sleep onset, sleep efficiency, number of wakeups, and duration of a sleep period. Further, when an individual has fallen asleep, it is desirable for guided breathing or relaxation exercises to gradually adjust and fade out so that the individual is not exposed to unnecessary stimuli. In aspects, when an individual has fallen asleep, it is desirable for masking sounds to be adjusted to protect the individual's sleep. When the individual is determined to be awake, it is desirable to decrease or pause masking sounds, trigger guided breathing or relaxation exercises to help the user fall back asleep, alter audio output according to the individual's preference, and/or prompt the user to stand up if the user is determined to be awake for a given amount of time.

Currently, population-level data is used to determine that a person is awake or asleep. In an example, based on human studies, physiological parameters are recorded when people are known to be asleep and awake. Population-level data is deployed for use with individual user devices. Sensor-collected data for an individual is compared with the population-level data to determine that a user is awake or asleep. While such approaches are helpful to gain an understanding of how long a user is asleep (e.g., the individual slept for approximately 8 hours during a sleep period), they are not robust enough to accurately determine in real-time, or virtually near real-time, when the user has fallen asleep or when the user wakes up.

One reason why the current methods do not support precisely determining sleep onset or wakeups is that individuals vary greatly in some physiological measures while awake and similarly individuals vary greatly in some physiological measures while asleep. Therefore, it is challenging to determine whether a specific person is asleep or awake using population-level data.

Figure 1:
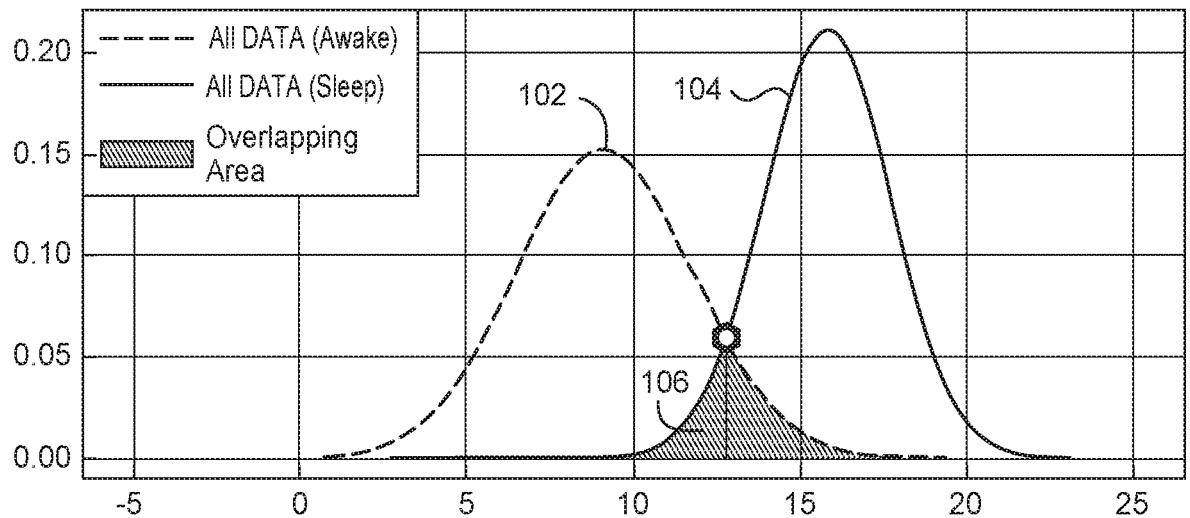
FIG. 1 illustrates an example population-level distribution of respiration rates during sleep and while awake.

FIG. 1 illustrates an example population-level distribution of respiration rates (RRs) 100 during sleep and awake times. The x-axis represents the population-level RR and the y-axis represents the proportion of time a plotted value is observed. Line 102 illustrates the distribution of RRs found in the population when awake. Line 104 illustrates the distribution of RRs found in the population when asleep. The region 106 represents the overlap of population-level awake RRs and population-level asleep RRs. Using population-level RRs as a physiological feature (parameter) to determine if a specific individual is asleep or awake is problematic, in part, because the distribution of RRs an individual exhibits, and consequently the population exhibits, when awake and asleep are wide and overlapping. Accordingly, awake and asleep values of the distribution of population-measured RRs may not clearly correlate with the distribution of an individual's awake and asleep RRs. As described herein, the distribution refers to the range of possible values as well as how often a measurement at a certain value is observed.

Figure 2:
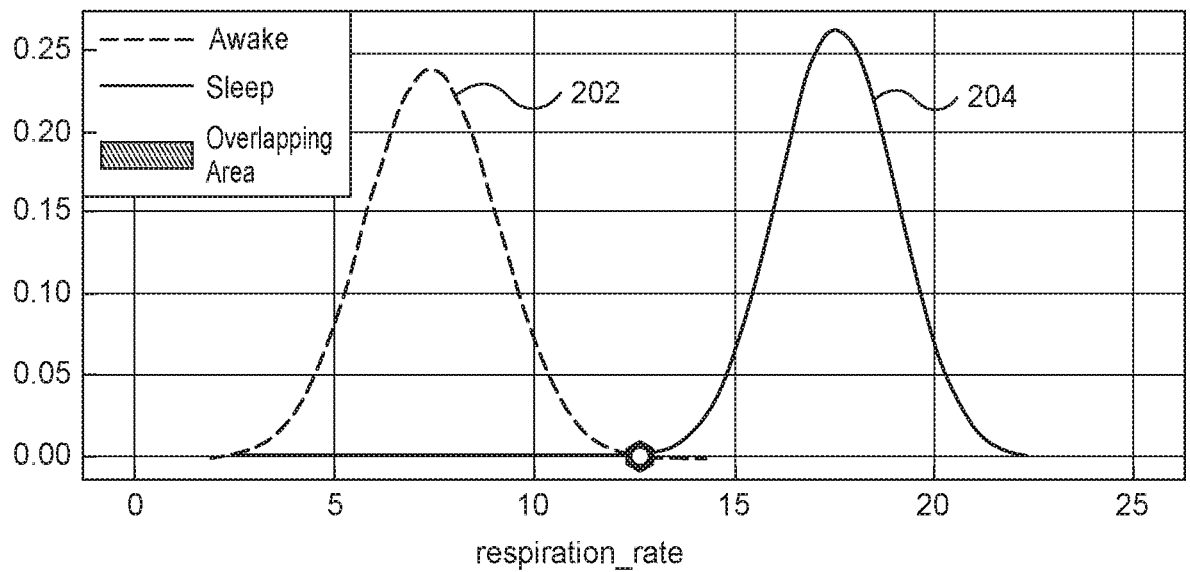
FIG. 2 illustrates an example distribution of the respiration rate of an individual while asleep and awake.

FIG. 2 illustrates an example distribution of the RRs of an individual 200 while asleep and awake. The x-axis represents the individual's RR and the y-axis represents the proportion of time a plotted value is observed for the individual. Line 202 illustrates the distribution of the individual's RR when awake. Line 204 illustrates the distribution of the individual's RR when asleep. In FIG. 2, there is little to no overlap between the distribution of RRs when the individual is awake and the distribution of RRs when the individual is asleep. Stated otherwise, on an individual-level, there is more separation between the distribution of awake RRs and the distribution of asleep RRs as compared to the population-level. Additionally, relative to FIG. 1, the distribution of the individual's RRs when awake or asleep is narrower than the population-level distribution of RRs when awake and asleep. Using an individual's personalized awake and asleep RRs more accurately indicates if the individual is awake or asleep. Further, based on the personalized awake and asleep distributions, sleep onset is more accurately determined.

FIGS. 1 and 2 refer to RR as an example of a measured physiological feature used to estimate when an individual is awake or asleep. Non-limiting examples of physiological features that can be measured at the population-level and individual-level to determine when a person is awake or asleep include a respiration signal, heart rate (HR), HR variability (HRV), body movements, and elements of breath architecture. Similarly, any other physiological feature that changes between wake and sleep can be used in accordance with the methods described herein. A respiration signal includes the different components of respiration including, for example, a RR and captures features of a heart signal. Breath architecture includes any combination of the ratio of time spent inhaling versus exhaling, how long a user breathes in, and the depth of the user's breath.

In one example, a device, such as an audio output device includes a memory and processor, communication unit, a transceiver, a sensor, and a speaker or audio output transducer. The audio output device is configured to collect and/or use personalized physiological parameters to precisely determine when a user falls asleep or awakes. Any or all of the components may be combined into multi-function components. In another example, the memory and processor, communication unit, transceiver, sensor, and speaker or audio output transducer are included in combination devices and/or the cloud in a sleeping environment. The devices communicate, in aspects, via a wired connection, the internet, or cloud-based communication, to perform the techniques described herein.

The memory may include Read Only Memory (ROM), a Random Access Memory (RAM), and/or a flash ROM. The memory stores program code for controlling the memory and processor. The memory and processor control the operations of the audio output device, and optionally, other devices in the sleep environment, as described herein.

The processor controls the general operation of the audio output device and/or other devices in the sleep environment. For example, the processor performs process and control for audio and/or data communication. The processor is configured to perform operations during the initialization stage using population-level data to determine when a user is awake or asleep, collect personalized physiological data, and correlate the collected personalized data with the user's awake or asleep state as described herein. After the initialization stage, the processor is further configured to direct operations during the steady-state stage using real-time sensor-collected data to determine the user has fallen asleep or has woken up as described herein.

In combination with the audio output transducer, the processor is configured to output audio which can take the form of a relaxation exercise, guided breathing exercise, or any other audio output either alone or in combination with, haptics or lights.

In at least one example, the processor is disposed on another device, such as a smartphone or audio output charging case and is in communication with the audio output device.

The audio output device optionally includes a communication unit that facilitates a wireless connection with one or more other wireless devices. The communication unit may include one or more wireless protocol engines such as a Bluetooth engine. While Bluetooth is used as an example protocol, other communication protocols may also be used. Some examples include Bluetooth Low Energy (BLE), NFC, IEEE 802.11, WiFi, or other local area network (LAN) or personal area network (PAN) protocols. In aspects, the communication unit receives information associated with the user's physiological parameters, obtained via a contactless sensor. Examples of contactless sensors include a radio frequency (RF) sensor, a radar sensor, or an under-bed accelerometer.

The transceiver transmits and receives information via one or more antennae to exchange information with one or more other wireless devices. The transceiver may be used to communicate with other devices in an audio system, such as a bedside unit, a smartphone, charging case, and/or a smartwatch. The transceiver is not necessarily a distinct component.

The audio output device includes the audio output transducer, which may be also known as a driver or speaker.

The audio output device optionally includes one or more sensors used to determine, sense, measure, monitor, or calculate a physiological feature of a subject wearing the audio output device. In an example, the sensor is an accelerometer, a PPG sensor, or a radar sensor. The accelerometer collects an accelerometer signal from which various physiological features are measured, estimated or extracted. The PPG sensor collects a PPG signal for which various physiological features are measured, estimated or extracted. The radar sensor collects a radar signal from which various physiological features are measured, estimated or extracted. Any sensor that collects a signal from which a physiological feature may be estimated to determine if a user is awake or asleep can be used in accordance with the methods described herein.

On a high-level, during the initialization period, a distribution of user-specific asleep values for a physiological feature when a user is determined to be asleep is determined. Additionally, a distribution of user-specific awake values for the physiological feature when the user is determined to be awake is determined. A sensor is used to measure values of the physiological feature to determine the distribution. Referring to FIG. 1, RR is an example of a physiological feature. In an example, the user's RR is measured and compared to the population-level distributions illustrated in FIG. 1. Based on the measured RR, the user is determined to be one of awake or asleep. Thereafter, one or more sensors measure the user's RR to determine a personalized distribution of RR for when the user is determined to be awake and determined to be asleep. During the initialization period, the method is learning the typical values of the physiological features a specific individual displays when awake and asleep, using population-level data as a starting point.

After completion of the initialization stage, the process shifts to a steady-state stage. On a high-level, during the steady-state stage, the user's real-time measured physiological features are compared with the user-specific distribution of values (as determined in the initialization stage) to determine if this specific user is awake or asleep. In response to determining the user is awake, the audio output device may begin an experience to guide the user to sleep. For example, the audio output device may initiate a relaxation or guided breathing exercise. In aspects, the experience includes audio in combination with visual output and/or haptic output. When the user is determined to be awake for a threshold amount of time (e.g., 20 minutes), the audio output device may coax the user to stand up through audio, visual, and/or haptic output, in an effort to promote healthy sleep hygiene. In response to determining the user has fallen asleep, one or more sensors on the audio output device or a device in communication with the audio output device may promptly enter a low-power mode. For example, a user experience may require the use of sensors on the audio output device. When the user is asleep, the experience may be paused. Accordingly, the device may save power when one or more components or sensors enter a low-power state. In aspects, when the user is determined to be asleep, the audio device may adjust an audio output in an effort to protect sleep and not expose the user to unnecessary stimulus.

Figure 3:
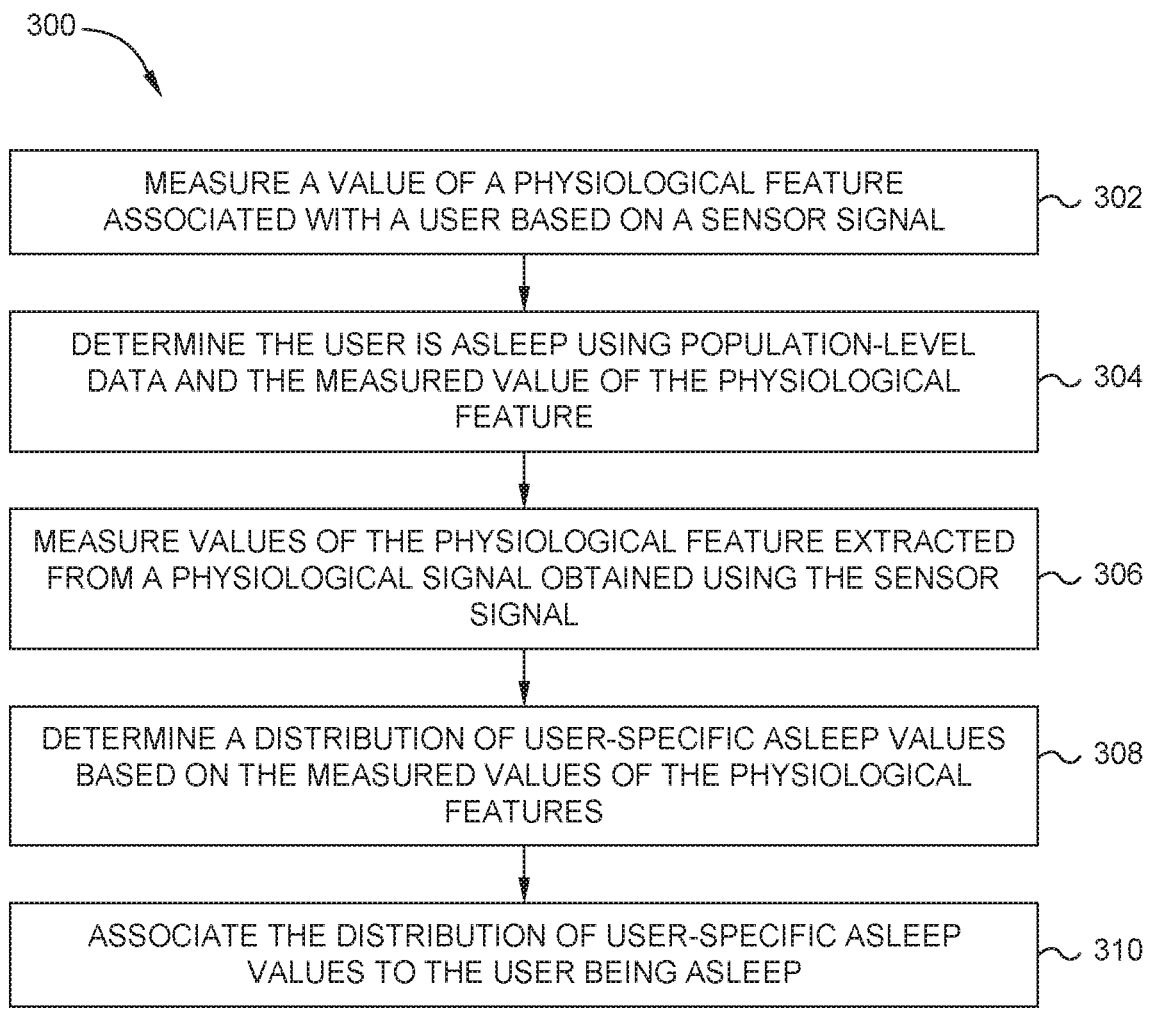
FIG. 3 illustrates example operations performed during an initialization stage, in accordance with aspects of the present disclosure.

FIG. 3 illustrates example operations 300 performed during an initialization stage, in accordance with aspects of the present disclosure. The operations 300 can be performed by any combination of the audio output device, a contactless sensor, a wireless device, and the cloud during an initialization period. The initialization period may last for a pre-determined amount of time, such as configured number of sleep periods or a configured number of days.

During an initialization period, a user's personalized physiological information is collected and compared to population-level data. Specifically, at 302, a value of a physiological feature associated with a user based on a sensor signal is measured. Example features include, a RR, ratio of time to inhale to time to exhale, depth of breath, HR, HRV, body movement, and/or or any other physiological feature that changes between wake and sleep. In aspects, one or more of an audio output device or a contactless sensor is used to measure the value of the physiological feature.

At 304, the user is determined to be asleep using population-level data and the measured value of the physiological feature. In an example, sensor data is compared to population-level data as illustrated in FIG. 1 and the user is determined to be asleep when the measured value of the physiological feature corresponds to an asleep value in the asleep distribution.

Given the user is determined to be asleep, at 306, a sensor obtains a sensor signal that is used to measure, determine, estimate, or extract values of the user's physiological feature from a physiological signal obtained using the sensor signal. At 308, a distribution of user-specific asleep values are determined using the measured values of the physiological features when the user is determined to be asleep (based on the population-level data from step 304). At 310, the distribution of personalized, user-specific asleep values are associated with the user being asleep. This distribution will be used in the steady-state stage as described with reference to FIG. 4 and FIG. 5 to provide the user with a timely, personalized audio experience.

According to aspects, the sensor signal comprises an accelerometer signal, a PPG signal, a radar signal, or any other sensor signal capable of detecting the physiological feature of interest. Regardless of the type of sensor signal, physiological parameters can be estimated, measured, or extracted from the sensor signal. In an example, the physiological signal is a respiration waveform.

Figure 4:
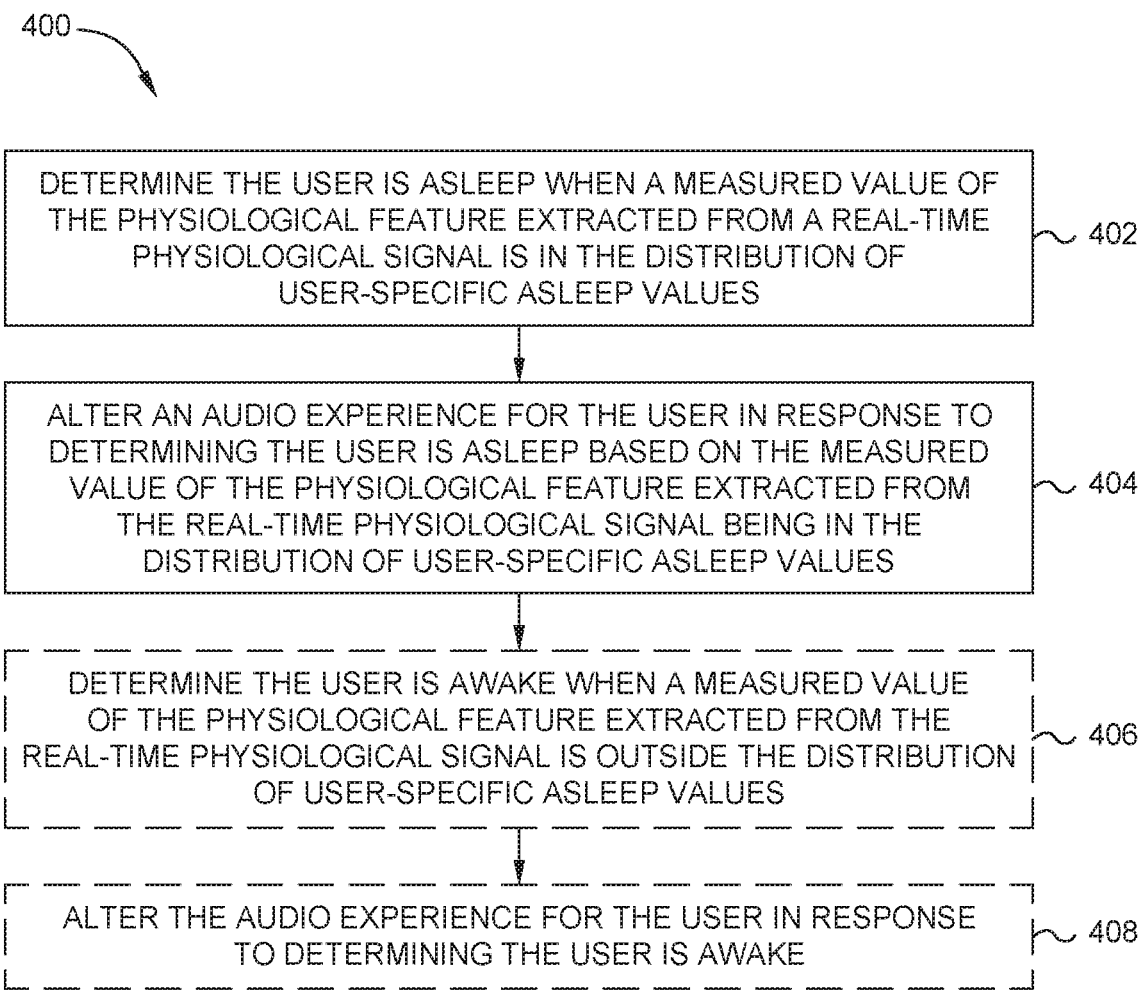
FIG. 4 illustrates example operations performed during a steady-state stage, in accordance with aspects of the present disclosure.

FIG. 4 illustrates example operations performed during a steady-state stage 400, in accordance with aspects of the present disclosure. The operations 400 can be performed by any combination of the audio output device, a contactless sensor, a wireless device, and the cloud. During the steady-state stage, the audio output device (or a device in communication with the audio output device) has acquired the user's personalized asleep and awake physiological distributions. The user's personalized data is used to precisely determine sleep onset and when the user wakes to provide the user with a timely, customized experiences and accurate health statistics.

At 402, the audio output device, wireless device, or the cloud determines the user is asleep when a measured value of the physiological feature extracted from a real-time physiological signal is in the distribution of user-specific asleep values (the user-specific values were calculated at 308 in FIG. 3). At 404, the audio experience for the user is altered based on determining the user is asleep.

Optionally, at 406, the audio output device, wireless device, or the cloud determines the user is awake when a measured value of the physiological feature extracted from the real-time physiological signal is outside the distribution of user-specific asleep values. Optionally, at 408, the audio output device alters the audio experience for the user in response to determining the user is awake. In aspects, when the user is determined to be awake steps are taken to help relax the user and guide the user back to sleep. In other aspects, the user is prompted to stand up. In aspects, based on the personalized determination of sleep onset and when the user wakes, more accurate sleep statistics are output. The sleep statistics can be used for potential health interventions and be used as additional information to guiding recommended therapies and content.

Figure 5:
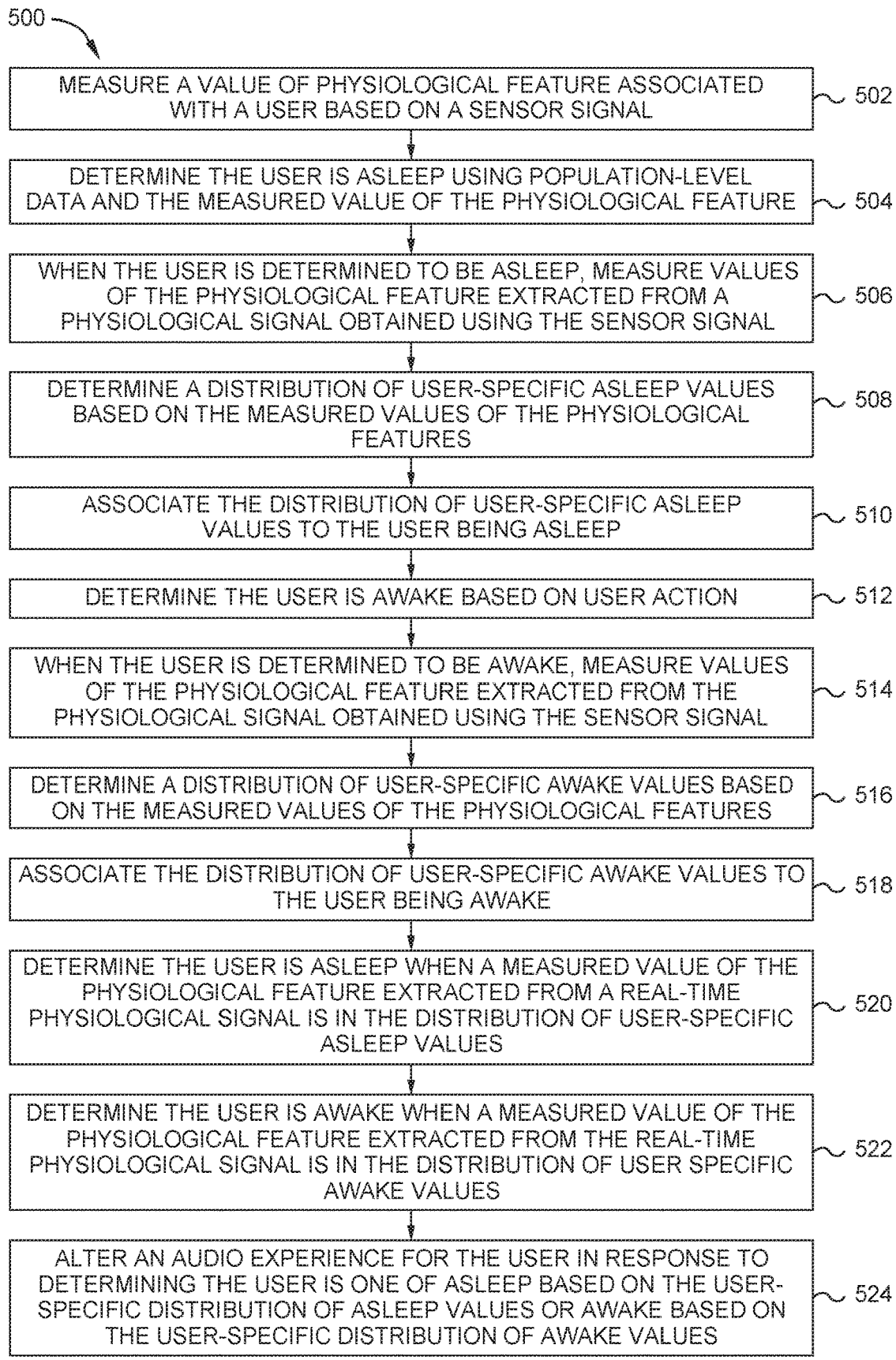
FIG. 5 illustrates example operations performed during the initialization stage and the steady-state stage, in accordance with aspects of the present disclosure.

FIG. 5 illustrates example operations 500 performed during the initialization stage and steady-state stage, in accordance with aspects of the present disclosure. The operations 500 can be performed by any combination of the audio output device, a contactless sensor, a wireless device, and the cloud.

Steps 502-518 occur during the initialization stage, when user-specific data is collected in order to determine personalized values of physiological parameters. Steps 520-524 occur during the steady-state stage, when real-time user-specific sensor data is used to determine the user is awake or asleep.

At 502, a sensor is used to measure a value of a physiological feature associated with a user based on a sensor signal. At 504, the user is determined to be asleep using population-level data and the measured value of the physiological feature. In aspects, the measured value of the physiological feature is compared to the population-level data to determine the user is asleep.

At 506, when the user is determined to be asleep, values of the physiological feature extracted from a physiological signal obtained using the sensor signal are measured. At 508, a distribution of user-specific asleep values based on the measured values of the physiological features are determined. At 510, the distribution of user-specific asleep values are associated with the user being asleep. These steps are similar to those described in FIG. 3.

At 512, the user is determined to be awake based on user action. At 514, when the user is determined to be awake, values of the physiological feature extracted from the physiological signal obtained using the sensor signal are measured. In aspects, user action includes the user interacting with the audio output device or wireless device (e.g., pressing a button, toggling through menus) or sensor collected data indicating the user is standing up.

At 516, a distribution of user-specific awake values based on the measured values of the physiological features are determined. At 518, the distribution of user-specific awake values are associated with the user being awake.

In an example, instead of using user action to determine the user is awake as shown in step 512, the user is determined to be asleep using population-level data and a measured value of a physiological feature. For example, a measured RR is compared to population-level data to determine the measured RR corresponds to an awake RR based on population-level data. Thereafter, the process proceeds to step 516 as described above.

After a predetermined amount of time has passed, the method transitions to the steady-state stage. In the steady-state stage, the audio output device, wireless device, or cloud has enough personalized physiological information, specific to the user, to identify when sleep onset has occurred or when the user is awake.

At 520, the user is determined to be asleep when a measured value of the physiological feature extracted from a real-time physiological signal is in the distribution of user-specific asleep values. At 522, the user is determined to be awake when a measured value of the physiological feature extracted from the real-time physiological signal is in the distribution of user-specific awake values. At 524, an audio experience is altered in response to determining the user is asleep based on the user-specific distribution of asleep values or awake based on the user-specific distribution of awake values.

Aspects of the present disclosure leverage population-level data to understand when a user is asleep or awake. Thereafter, user-specific physiological features are measured to understand precisely when the user is awake or asleep. In some cases, the techniques described herein accurately determine, by the minute, when the user has fallen asleep or woken up. After personalized data is collected over a period of time, the user's distribution of awake and asleep physiological parameters are known. Thereafter, the method determines the user is awake or asleep based on the user's determined distribution instead of the population-level data to provide a tailored user experience and more accurate sleep statistics.

In the preceding, reference is made to aspects presented in this disclosure. However, the scope of the present disclosure is not limited to specific described aspects. Aspects of the present disclosure may take the form of an entirely hardware embodiment, an entirely software embodiment (including firmware, resident software, micro-code, etc.) or an embodiment combining software and hardware aspects that may all generally be referred to herein as a "component," "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium include: an electrical connection having one or more wires, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the current context, a computer readable storage medium may be any tangible medium that can contain, or store a program.

The flowchart and block diagrams in the figures illustrate the architecture, functionality and operation of possible implementations of systems, methods and computer program products according to various aspects. In this regard, each block in the flowchart or block diagrams may represent a module, segment or portion of code, which comprises one or more executable instructions for implementing the specified logical function(s). In some implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustrations, and combinations of blocks in the block diagrams and/or flowchart illustrations can be implemented by special-purpose hardware-based systems that perform the specified functions or acts, or combinations of special purpose hardware and computer instructions.

The invention claimed is:

1. A method for creating a personalized audio experience to promote sleep health, comprising:
   determining a distribution of user-specific asleep values for a physiological feature when a user is determined to be asleep;
   determining a distribution of user-specific awake values for the physiological feature when the user is determined to be awake;
   determining the user is asleep when a measured value of the physiological feature extracted from a real-time physiological signal is in the distribution of user-specific asleep values;
   determining the user is awake when a measured value of the physiological feature extracted from the real-time physiological signal is in the distribution of user-specific awake values;
   determining the user has been awake for a threshold amount of time; and
   altering an audio experience based on determining the user is asleep or awake via the measured value of the physiological feature being in the distribution of user-specific awake values or the user-specific asleep values, wherein altering the audio experience comprises instructing the user to stand up, via at least one of audio, video, or haptic output, when the user is determined to be awake for the threshold amount of time.

2. The method of claim 1, further comprising:
   entering a low-power mode by one or more sensors in response to determining the user is asleep.

3. A method for creating a personalized audio experience to promote sleep health, comprising:
   during an initialization stage:
      measuring a value of a physiological feature associated with a user based on a sensor signal;
      determining the user is asleep using population-level data and the measured value of the physiological feature;
      when the user is determined to be asleep, measuring values of the physiological feature extracted from a physiological signal obtained using the sensor signal;
      determining a distribution of user-specific asleep values based on the measured values of the physiological features to create a more personalized distribution of asleep values as compared to the population-level data; and
      associating the distribution of user-specific asleep values to the user being asleep; and
   after the initialization stage:

determining the user is awake when a measured value of the physiological feature extracted from the real-time physiological signal is outside the distribution of user-specific asleep values; and altering an audio experience for the user in response to determining the user is awake based on the measured value of the physiological feature extracted from the real-time physiological signal being outside the distribution of user-specific asleep values, wherein altering the audio experience comprises instructing the user to stand up, via at least one of audio, video, or haptic output, when the user is determined to be awake.

4. The method of claim 3, wherein the sensor signal comprises one of: an accelerometer signal, photoplethysmogram (PPG) signal, a radar signal, or any other sensor signal capable of detecting the physiological feature.

5. The method of claim 3, wherein the physiological signal is a respiration waveform.

6. The method of claim 3, wherein the physiological feature comprises one of:
a respiration rate (RR), ratio of time to inhale to time to exhale, depth of breath, heart rate (HR), heart rate variability (HRV), body movement, or any other physiological feature that changes between wake and sleep.

7. The method of claim 3, wherein the initialization stage lasts for a pre-determined amount of time.

8. The method of claim 3, further comprising:
outputting at least one of: time-to-sleep onset or how many times the user awoke during a sleep period.

9. A method for creating a personalized audio experience to promote sleep health, comprising:
during an initialization stage:
determining a user is awake based on user action;
when the user is determined to be awake, measuring values of a physiological feature extracted from a physiological signal obtained using a sensor signal;
determining a distribution of user-specific awake values based on the measured values of the physiological feature to create a more personalized distribution of awake values as compared to the population-level data; and
associating the distribution of user-specific awake values to the user being awake; and
after the initialization stage:
determining the user is awake when a measured value of the physiological feature extracted from the real-time physiological signal is in the distribution of user-specific awake values;
determining the user has been awake for a threshold amount of time; and
altering an audio experience for the user in response to determining the user is one of asleep based on the user-specific distribution of asleep values or awake based on the user-specific distribution of awake values, wherein altering the audio experience comprises instructing the user to stand up via at least one of audio, video, or haptic output.

10. The method of claim 9, wherein the sensor signal comprises one of: an accelerometer signal, photoplethysmogram (PPG) signal, a radar signal, or any other sensor signal capable of detecting the physiological feature.

11. The method of claim 9, wherein the physiological signal is a respiration waveform.

12. The method of claim 9, wherein the physiological feature comprises one of:
a respiration rate (RR), ratio of time to inhale to time to exhale, depth of breath, heart rate (HR), heart rate variability (HRV), body movement or any other physiological feature that changes between wake and sleep.

* * * * *